United States Patent [19]
Dougherty et al.

[11] 3,933,930
[45] Jan. 20, 1976

[54] HEXANEDIOL FROM CYCLOHEXANE

[75] Inventors: Edward F. Dougherty; Charles C. Hobbs, Jr., both of Corpus Christi, Tex.

[73] Assignee: Celanese Corporation, New York, N.Y.

[22] Filed: Mar. 6, 1975

[21] Appl. No.: 555,920

[52] U.S. Cl............ 260/635 D; 23/289; 260/631 R; 260/631 H; 260/666 A; 260/666 P
[51] Int. Cl.².......................................... C07C 29/00
[58] Field of Search................................ 260/635 D

[56] References Cited
UNITED STATES PATENTS

| | | | |
|---|---|---|---|
| 2,904,584 | 9/1959 | Payne et al. | 260/635 D |
| 3,268,588 | 8/1966 | Horlenko et al. | 260/635 D |
| 3,432,560 | 3/1969 | Martin et al. | 260/635 D |

*Primary Examiner*—Joseph E. Evans
*Attorney, Agent, or Firm*—Stewart N. Rice; Ralph M. Pritchett

[57] ABSTRACT

In the production of 1,6-hexanediol by oxidation of cyclohexane to produce an acidic oxidation product comprising adipic acid, followed by esterification of the acidic oxidation product and a subsequent hydrogenolysis of the ester, the improvement which comprises a prehydrogenation of the acidic oxidation product prior to esterification thereof.

6 Claims, No Drawings

HEXANEDIOL FROM CYCLOHEXANE

BACKGROUND OF THE INVENTION

The present invention relates to the production of 1,6-hexanediol from cyclohexane. The basic process for such is well known by the following general procedure: cyclohexane is oxidized to produce an acid product including predominantly adipic acid and 6-hydroxyhexanoic acid; the acid product is esterified with an alkanediol and the esters are hydrogenolyzed to 1,6-hexanediol and the said alkanediol. 1,6-hexanediol is useful in that it may be aminated to produce hexamethylenediamine, the latter being a starting reagent for 6,6 nylon. Production of 1,6-hexanediol from cyclohexane is, for example, more particularly described in U.S. Pat. No. 3,524,892 issued Aug. 18, 1970 to Horlenko et al.

In the oxidation of cyclohexane, the main oxidation products consist of cyclohexanone, cyclohexanol, adipic acid, epsilon-caprolactone and 6-hydroxyhexanoic acid. However, various other oxygenated hydrocarbons are also formed such as 1,4-dihydroxycyclohexane; various aldehydes such as adipaldehydic acid, adipaldehyde; various ketones such as levulinic acid; and various $C_1$-$C_6$ monocarboxylic and dicarboxylic acids other than those already mentioned, such as glutaric, succinic, formic, and 3-hydroxyadipic. As hereinafter explained, a non-acid fraction comprising the cyclohexanone and cyclohexanol is separated from the reaction product and may be recycled to the oxidation reactor if desired.

In the oxidation of the cyclohexane, air is suitably utilized as the source of molecular oxygen, but other suitable oxygencontaining gaseous mixtures, or substantially pure oxygen itself, may be utilized. The oxidation takes place at elevated temperatures and superatmospheric pressures sufficient to maintain a liquid phase of the cyclohexane as well as any recycled cyclohexanol and cyclohexanone.

Although it is not absolutely necessary, it is convenient to use an oxidation catalyst of any of the well known types generally employed in oxidation. Catalyst systems which work particularly well contain a metal which exists in at least two valence states, such as for example, cobalt, manganese, iron, chromium, nickel or copper. It is preferred to employ these metals in compound form, salts for example, although they can be used in the uncombined state. Cobalt naphthenate and cobalt acetate have been found to be particularly useful in the practice of the invention. Catalysts can be used in the proportion of metal to reaction mixture of 1 to 500 parts per million, preferably less than about 100 parts per million, e.g. 5 to 15 ppm. Of these catalysts, the naphthenate is the more hydrocarbon-soluble.

Since there is some tendency for some of the oxidation reaction products to polymerize, it is best to inhibit this propensity where possible. The extent of polymerization of both 6-hydroxyhexanoic acid and epsilon-caprolactone can be reduced by the addition of a minor amount of water to the reaction mass. This water can be suitably retained in the reaction mass by means of a reflux condenser which will return volatilized water to the reaction mass. This condenser also serves to retain volatilized constituents of the reaction mass, cyclohexane, cyclohexanone and cyclohexanol, in the reaction zone. It has been found that about 2 to 10 percent by weight of water in the reaction mass is convenient to reduce polymerization of the reaction products.

The oxidation reaction temperature is suitably maintained between about 100° and 200°C. Temperatures below about 160°C and preferably below about 140°C have been found to be best for oxidation according to this invention. Oxidation reaction pressure is conveniently in the range of 4 to 50 atmospheres absolute, preferably about 8 to 40 atmospheres absolute, which pressure is suitably maintained by bubbling the oxidizing gas through a liquid reaction mass while permitting spent oxidizing gases to escape at such a rate as to maintain the desired pressure.

It is practical to pass the desired oxidation products, including 6-hydroxyhexanoic acid, adipic acid, adipaldehydic acid and epsilon-caprolactone, directly into an esterification stage. It is also convenient to separate the oxidation product into an acid fraction suitable for esterification and a nonacid fraction for recycle. This can be accomplished by extracting the reaction products with water to form an aqueous phase containing the desired oxidation products to be esterified and a hydrocarbon phase containing the oxidation products and reactants to be recycled. The aqueous phase is then distilled to recover cyclohexanol and cyclohexanone for recycle or as salable products. While it is preferred to extract the oxidation product with water, it is within the scope of this invention to subject the oxidation products to distillation without first water extracting the 6-hydroxyhexanoic acid, adipic acid and epsilon-caprolactone therefrom. The ratio of water to reaction mixture in the extraction operation should be at least 1 to 4, preferably from about 1 to 4 to about 5 to 6. Extraction is conveniently carried out above room temperature, 30 to 150°C being adequate and 50 to 100°C being preferred.

The water extract is permitted to settle into an aqueous phase and a hydrocarbon phase, the hydrocarbon phase containing cyclohexanone, cyclohexanol and cyclohexane and the aqueous phase containing 6-hydroxyhexanoic acid, adipic acid, cyclohexanone, cyclohexanol and epsilon-caprolactone. The hydrocarbon phase is recycled to the oxidation reactor and the aqueous phase is distilled to remove any cyclohexanone and cyclohexanol as water azeotropes, which distillate may be returned to the oxidation reaction, leaving 6-hydroxyhexanoic acid, adipic acid, epsilon-caprolactone, and other acid and ester oxidation products to be esterified.

In the alternative, the above described water extraction operation can be foregone and the oxidation reaction products can be passed directly to a distillation step in which the water, cyclohexane, cyclohexanone and cyclohexanol are stripped off overhead, preferably azeotropically, and returned to the oxidation operation leaving behind an aqueous residue containing 6-hydroxyhexanoic acid, adipic acid, epsilon-caprolactone and other acid products. In this alternative procedure, it is desirable to add water to the distillation operation with the oxidation reaction products in order to have sufficient water present to azeotrope with the fraction to be recycled. Additionally, the excess water present in the distillation operation tends to inhibit the polymerization of 6-hydroxyhexanoic acid and epsilon-caprolactone and also reduces the extent of esterification of the acid products such as adipic, glutaric or succinic acid by the cyclohexanol which is present. It is practical to use either atmospheric or reduced pressure at temperatures ranging from about 50° to 100°C in the distillation discussed above.

Another alternative procedure for removing the cyclohexanone and cyclohexanol in the aqueous phase of the extracted oxidation product is by liquid-liquid extraction with cyclohexane at about 25° to 100°C. The cyclohexanone and cyclohexanol in the cyclohexane extraction product are suitably removed, e.g. by distillation or other techniques.

Although it is possible to produce adipic acid, 6-hydroxyhexanoic acid and epsilon-caprolactone by batch oxidation of cyclohexane, cyclohexanol and cyclohexanone, it is much more desirable to operate continuously. It is convenient to use a "back-mixing" type of reactor wherein there is thorough agitation of the reaction mixture while an oxidizing gas is being bubbled through the reaction mixture and wherein cyclohexane is being continuously fed into the reactor, reaction product is continuously being tapped off and cyclohexanone, cyclohexanol and cyclohexane are continuously being recycled to the reactor.

The esterification of the acid fraction of the oxidation product (e.g. 6-hydroxyhexanoic acid, epsilon-caprolactone, adipic acid, glutaric acid and succinic acid) can be carried out catalytically or non-catalytically. In the instant invention, it is preferred to esterify non-catalytically. The esterification is suitably carried out with substantially any monohydric or polyhydric hydroxyl containing compound which is thermally stable at temperatures in excess of 150°C, a $C_2$-$C_{10}$ monohydric or dihydric alkane alcohol generally being used. The hydroxyl containing compound must have a boiling point high enough to be non-volatile during the non-catalytic esterification reaction at the pressure being used. Hydroxyl containing compounds which are useful in this invention are exemplified by n-decyl alcohol, propylene glycol, 1,6-hexanediol (especially preferred), 1,4-butanediol, 1,5-pentanediol, ethanol, methanol, and n-butanol, the latter three alcohols being esterified under pressure. It is preferred to use a $C_3$-$C_{10}$ alkanediol, for example 1,6-hexanediol or 1,5-pentanediol or mixtures thereof.

It is convenient to carry out the esterification operation in one or more distillation columns. In one embodiment of this invention, the acid products of oxidation referred to above are mixed with an esterifying alcohol, glycol or polyol and introduced into a distillation column which operates at about atmospheric pressure until a pot temperature of about 160° to 200°C is realized whereupon the temperature is maintained by reducing the pressure to about 100 mm. Hg absolute and then the temperature is permitted to climb to about 250°C. The product is taken as a liquid stream from the base of the column and the water and other volatiles are taken overhead. Part of the base product is recycled to the first column and part introduced into a second column where further esterification takes place. The product of the second column is taken as a base stream, part refluxed and part passed to a third column where the ester product and any unreacted esterification alcohol or polyol are separated from any water present. The water is taken overhead, part refluxed to the column and part taken out of the process to be sewered or used elsewhere. The ester product and unreacted esterification alcohol are taken as a base stream and sent to a column in which the unreacted alcohol or polyol is separated from the esterification product.

Where 1,6-hexanediol is the esterifying alcohol, non-catalytic esterification takes place at about 100 mm. Hg absolute to atmospheric pressure, at a temperature of about 150° to 250°C, and a mole ratio of about 0.5 to 1 to 10 to 1 alcohol to acid. It is preferred to operate at about 200°C at an alcohol to acid ratio of about 3 to 1. In the first embodiment set forth above wherein a two column series esterification is utilized in combination with a third column separation unit, the first 80% or so of the esterification takes place in these first two columns, the combined residence times in these columns being about 2 hours. Conversions as high as 95%, based upon acids fed, have been realized in the esterification operation. In this embodiment, the third esterification column operates at a reflux ratio of 2 to 1 and the water overhead is taken at 100 mm. Hg absolute. The column used to separate unreacted alcohol from ester product is conveniently operated at a 1 to 1 reflux ratio of about 10 mm. Hg absolute. The product of esterification generally contains about 60% ester, 35% alcohol, 0.8% acid and 0.2% water. The ester has a high viscosity and an amber color.

The ester product, is hydrogenolyzed to break the ester bond thereby regenerating the esterifying hydroxyl compound and hydrogenolyzing the carboxyl moieties to their corresponding alcohols, e.g. 1,6-hexanediol, 1,5-pentanediol, 1,4-butanediol, n-hexanol and cyclohexanol. The hydrogenolysis can be advantageously carried out by feeding the esterification product and hydrogen to a reactor maintained at about 200° to 350°C and 70 to 900 atmospheres absolute, preferably 250° to 290°C and 250 to 350 atmospheres absolute. The reactor contains a hydrogenolysis catalyst. Substantially any of the catalysts known for hydrogenation or hydrogenolysis are operable such as those of copper, cobalt, platinum, palladium, or nickel; however, copper chromite, barium stablized copper chromite, Raney copper and barium oxide promoted copper chromite have been found to be particularly well suited to this process since they are not poisoned to any great extent during the process. Suitably, the catalyst may be supported by an inert carrier, e.g. pumice or inactive alumina. Inactive alumina is alumina hydrate which has been calcined at between about 1000°C and the melting point of alumina. In investigating the parameters of this invention, it was found that barium oxide stabilized copper chromite catalyzed the hydrogenolysis to 80% or higher conversions. It is practical to carry out the hydrogenolysis either with or without a solvent. Where a solvent is used, dioxane has been found to work well as have butanol and ethanol. The solvent is admixed with the esters at about 100° to 150°C; the mixture then heated to about 190°C in a closed vessel; and then fed into the hydrogenolysis reactor. The proportion of solvent to ester in the feed is about 1 to 4 to 2 to 1, preferably about 1 to 1.

The hydrogenolysis reaction can be carried out in either a fixed, flooded catalyst bed, a slurry catalyst bed or a trickle catalyst bed. In any case, the heat of reaction brings the reaction mass up to a temperature of about 245° to 250°C and the feed hydrogen supplies the pressure necessary for hydrogenolysis. A fixed, flooded catalyst bed is one in which the particles of catalyst are substantially pelletized or in some other relatively large form wherein the liquid phase material being acted on by the catalyst is a continuous phase which completely submerges the catalyst bed. A fixed trickle catalyst bed is one in which the particles of catalyst are generally pelletized and placed in a relatively fixed position with the liquid phase material being acted on by the catalyst being fed at the top of the bed and forming a relatively discontinuous phase. A slurry bed catalyst consists of powdered catalyst, e.g. about 60 microns or less, with the liquid phase being acted upon flooding the catalyst bed and floating the powdered catalyst. In the slurry bed catalyst it is usual to introduce the liquid at the bottom of the bed; in the trickle bed catalyst, it is usual to introduce the liquid at the top of the catalyst bed; and in the flooded fixed bed catalyst the liquid can conveniently be fed at top or bottom although the bottom is preferred. In each case, the gas phase is introduced at the bottom of the catalyst bed and bubbled through a slurry or fixed flooded bed catalyst, or forms a continuous phase through which liquid trickles. In bubbling gas through liquid, it is best to keep the gas bubbles small in order to maximize the ratio of surface area to volume of each bubble.

It is preferred that the hydrogenolysis catalyst life is such as to produce at least about 100 pounds of alcohol hydrogenolysis product per pound of catalyst. A catalyst life such that 200 pounds of diol product per pound of catalyst is made would of course be greatly desirable.

The hydrogenolysis product is taken as a base stream from the reactor and passed through a purification operation to separate the various products. Before the hydrogenolysis product is passed to the purification operation, it is let down in pressure to a pressure within the range of about atmospheric pressure to 10 atmospheres absolute in order to permit dissolved hydrogen to escape, which hydrogen may be recycled. The hydrogenolysis reactor is vented overhead thereby maintaining the required pressure with the hydrogen thus passed off either being permitted to escape to the atmosphere, recycled into the hydrogen feed or used elsewhere.

Where a solvent is used, the hydrogenolysis product is distilled to remove the solvent overhead with the alcohol products being taken as a base stream. In either case, where solvent is used and distilled off or where no solvent is used, the hydrogenolysis product alcohols substantially free of solvent are subjected to successive distillations to separate the products. The first column is preferably operated at about 20 to 10 mm. Hg absolute and 160° to 200°C to remove the substantially pure mixture of alcohols from undesirable high boilers. The mixed alcohols are taken overhead and passed into a second column which operates at about 20 mm. Hg absolute with a pot temperature of about 200°C and a vapor temperature of about 145° to 146°C to remove 1,5-pentanediol and 1,4-butanediol overhead. The base stream from this column is passed into a third distillation column operating at about 155° to 170°C and 20 to 44 mm. Hg absolute to purify the 1,6-hexanediol which is taken overhead and surged to heated vessels and thence part recycled to the esterification operation referred to above and part recovered as product. The base stream from the third still can be sewered or separated and purified to recover any valuable products therefrom.

Although the above described procedure for production of 1,6-hexanediol from cyclohexane is utilized commercially, it undesirably results in a 1,6-hexanediol which is contaminated with various undesirable impurities that are not readily separable therefrom. Further, some of these impurities are produced at the expense of otherwise obtainable 1,6-hexanediol. The cyclohexane oxidation itself is the source of the impurities, there being produced in the cyclohexane oxidation such undesirable impurities as 1,4-dihydroxycyclohexane, various aldehydes such as adipaldehyde, various ketones such as levulinic acid and other components such as 3-hydroxyadipic acid. Such impurities eventually end up in the acid fraction which is esterified and they (or some derivative thereof) ultimately end up, in part, in the 1,6-hexanediol product. 1,4-dihydroxycyclohexane and its precursors are perhaps the most prevalent and most troublesome impurities produced in the oxidation. These latter impurities are about 50% destroyed in the esterification process but the remainder largely winds up in the 1,6-hexanediol product as 1,4-dihydroxycyclohexane.

The aldehydes and ketones produced in the oxidation go, respectively, to acetals and ketals during the esterification. Except for cyclohexanone derivatives, ketals are probably formed to a much smaller extent than acetals. Both acetals and ketals are converted to undesirable esters during hydrogenolysis. The 3-hydroxyadipic acid produced in the oxidation may be converted during the process to a triol or other high boiler which is undesired.

It is thus an object of the present invention to provide an improved process for the production of 1,6-hexanediol from cyclohexane. It is a particular object of the present invention to provide a processing step which, in a process for producing 1,6-hexanediol from cyclohexane, will result in a purer 1,6-hexanediol product. It is also an object of the present invention to provide a process for producing 1,6-hexanediol from cyclohexane wherein a greater efficiency is obtained. Additional objects will become apparent from the following description of the present invention.

SUMMARY

The foregoing and additional objects are accomplished by the present invention which in one of its aspects is an improvement in a process for the production of 1,6-hexanediol from cyclohexane wherein: (a) cyclohexane is oxidized in the liquid phase in the presence of molecular oxygen and an oxidation catalyst at elevated temperatures and superatmospheric pressures to produce an oxidation product; (b) said oxidation product is separated into a non-acid fraction comprising cyclohexanol or cyclohexanone or mixtures thereof and an acid fraction comprising substantially adipic acid and 6-hydroxyhexanoic acid, said acid fraction also containing $C_1$ to $C_6$ monocarboxylic and dicarboxylic acids as well as 1,4-dihydroxycyclohexane and/or precursors thereof; (c) said acid fraction is esterified by reacting same in the liquid phase with a $C_2$-$C_{10}$ monohydric or dihydric alkane alcohol under esterification conditions so as to esterify at least a portion of the adipic acid and 6-hydroxyhexanioc acid contained in said acid fraction; (d) the ester product obtained by esterifying said acid fraction is reacted while in a liquid phase with molecular hydrogen under hydrogenolysis conditions including elevated temperature and superatmospheric pressure and in the presence of a catalytic amount of a hydrogenolysis catalyst to hydrogenolyze the esters of adipic acid and 6-hydroxyhexanoic acid so as to form 1,6-hexanediol and said alkane alcohol; and (e) separating 1,6-hexanediol from the product of said hydrogenolysis; which improvement comprises a prehydrogenation of said acid fraction prior to esterification thereof by reacting said acid fraction while in a liquid phase with molecular hydrogen under hydrogenation conditions including elevated temperature and superatmospheric pressure and in the presence of a catalytic amount of a hydrogenation catalyst to a degree sufficient to convert a substantial portion of said 1,4-dihydroxycyclohexane to cyclohexanol, cyclohexane and/or cyclohexene, but insufficient to appreciably hydrogenolyze the adipic acid and 6-hydroxyhexanoic acid therein.

DETAILED DESCRIPTION OF THE INVENTION

The improvement of the present invention comprises a prehydrogenation of the acid fraction sent to esterification. It has been discovered that this prehydrogenation improves the efficiency to an ultimate product of improved purity by converting the above mentioned impurities to compounds which may be easily removed or to components which are subsequently converted to product. For example, in the prehydrogenation 1,4-dihydroxycyclohexane is converted to cyclohexanol, cyclohexane and cyclohexene, which may readily be separated. A compound such as 3-hydroxyadipic acid is converted during the prehydrogenation to adipic acid or perhaps to a hexenedioic acid, which are desired compounds. Prehydrogenation of the acid fraction also converts the aldehydes and ketones, such as adipaldehydic acid and levulinic acid, to 6-hydroxyhexanoic acid and (probably) valeric acid or gamma-valerolactone, respectively, which are either desirable compounds or generate impurities which are easily removed.

The prehydrogenation is not as severe or carried out to the same degree as the hydrogenolysis step wherein the adipic acid esters are hydrogenolyzed to 1,6-hexanediol. Since the purpose of the prehydrogenation is to remove components which undergo undesirable reactions in the esterification or generate difficulty removable impurities, it should only be carried out to a degree sufficient to convert a substantial portion of the 1,4-dihyroxycyclohexane to cyclohexanol, cyclohexane and cyclohexene, but insufficient to appreciably hydrogenolyze the adipic acid present. Carrying the prehydrogenation to such degree will also result in the desired effect on the other impurities such as 3-hydroxyadipic acid and the like.

The prehydrogenation can generally be carried out by the same general methods already disclosed for the hydrogenolysis of the ester product, and generally the same type catalysts may be used except that nickel catalysts are not desirable. Preferably the catalyst is of copper, cobalt, platinum or palladium or mixtures thereof. In the prehydrogenation, a metallic copper or metallic platinum catalyst is especially preferred. In some instances, the catalyst may be prepared in situ, such as by reduction of a metal salt under hydrogenation conditions, although an ex situ reduction will also provide a suitable catalyst. Metal salts that may be reduced include the acetates, nitrates, various complexes and the like, for example, copper acetate. The actual metal itself, such as a screen of copper wire, is also effective, though not preferred. A substantially completely activated (that is at least 90% aluminum removal) Raney metal catalyst is also suitable.

The prehydrogenation should be carried out at temperatures within the range of 100° to 350°C, preferably 150° to 275°C, and at pressures within the range of 50 to 400 atmospheres absolute, preferably 70 to 300 atmospheres absolute. Residence times may vary widely depending on the amount and type of catalyst used, etc. In general the residence times will be on the order of from 30 to 240 minutes.

Following the prehydrogenation of the acid fraction, it can be passed directly to the esterification.

EXAMPLE 1

A hydrogenation reduction system was employed which comprised a two-liter stainless steel rocking autoclave, provided with means for measuring and controlling the internal temperature and hydrogen pressure.

The autoclave was packed with 100 grams of copper strips (0.0127 × 0.4 × 46 cm). A copper coating was deposited on the interior of the reactor and on the copper strips by charging the autoclave with approximately 0.5 liter of a 10% by weight copper acetate solution in water and then, with the autoclave being rocked, subjecting its contents to hydrogen at a pressure of about 200 atmospheres absolute and a temperature of 180°C for 4 hours. At the end of this time, the reactor was opened and drained. Visual examination indicated that the copper strips and the internal walls of the reactor were coated with a reddish layer of copper crystals.

The reactor was next charged with 0.5 liter sample of a water-diluted (40% total water by weight) acid fraction obtained from the oxidation product of a cyclohexane oxidation wherein cyclohexane had been oxidized in the liquid phase with air in the presence of a cobalt naphthenate catalyst at a temperature of about 145°C and a pressure of about 35 atmospheres absolute. Except for the 40% water of dilution, the sample comprised mainly adipic acid and 6-hydroxyhexanoic acid, although minor amounts of undesirable impurities such as 3-hydroxyadipic acid, formic acid, various formates, 1,4-dihydroxycyclohexane and various organic carbonyl compounds were present. A hydrogen atmosphere at approximately 300 atmospheres absolute pressure was applied, the internal temperature was adjusted to approximately 265°C, and the reactor was agitated by rocking under these conditions for approximately four hours. At the end of this period, the reactor was allowed to cool, the hydrogen atmosphere was released, and liquid product solution was analyzed. Analysis indicated that the 3-hydroxyadipic acid, formic acid, formates, and 1,4-dihydroxycyclohexane were substantially completely removed. The carbonyl content was reduced by greater than 90%. Adipic and 6-hydroxyhexanoic acids (1,6-hexanediol potential) increased 20%.

After such prehydrogenation, 500 grams of the liquid product solution of the prehydrogenation was mixed with 300 grams of 1,5-pentanediol. The mixture was charged to a 30-tray Oldershaw distillation column and allowed to esterify noncatalytically at 240°C and 1 atmosphere of pressure for 2 hours. During this time, water and some volatiles were taken overhead. At the end of two hours, the pressure was reduced to 180 mm Hg absolute and additional water of esterification removed. The product of esterification contained by weight about 60% ester, 35% alcohol, 0.8% acid (all at molecular weight 100), and 0.2% $H_2O$.

500 grams of this ester product was blended with 500 grams of 1,4-dioxane and 80 grams of barium stabilized copper chromite. This mixture was charged to a stainless steel rocking autoclave provided with means for measuring and controlling the internal temperature and pressure and was allowed to react with hydrogen at 250°C and 4500 psig for 6 hours so as to hydrogenolyze the ester. At the end of this time, the reaction was essentially complete. The diol product was removed and centrifuged to remove the hydrogenolysis catalyst.

The catalyst-free diol product is fed continuously to a three-column Oldershaw distillation system. The first column provides for removal of the light ends overhead. The residue is fed to a second column where diols are removed overhead and high boilers are removed in the base. The overhead product, containing diols, is fed to the lower-middle of a third tower. 1,6-Hexanediol is removed as a vapor side stream; other diols are removed overhead. Per gram of the ester product above, 0.50 gram of 1,6-hexanediol is isolated in the product side stream. This is approximately a 20% increase in 1,6-hexanediol yield when compared to a process wherein the water-diluted acid fraction sample is not hydrogenated prior to esterification and hydrogenolysis.

EXAMPLE II

The procedure described in Example I was repeated, except, in place of copper strips, the autoclave was packed with carbon pellets. Copper plating procedure, feedstock, and hydrogenation procedures were the same as in Example I. Results were essentially the same.

EXAMPLE III

Example I was repeated except the catalyst was changed to 100 grams of 5% by weight platinum on carbon. Results were the same.

The embodiments of the invention in which an exclusive property or privilege is claimed are defined as follows:

1. In a process for the production of 1,6-hexanediol from cyclohexane wherein:
    a. cyclohexane is oxidized in the liquid phase in the presence of molecular oxygen and an oxidation catalyst at elevated temperatures and superatmospheric pressures to produce an oxidation product;
    b. said oxidation product is separated into a non-acid fraction comprising cyclohexanol or cyclohexanone or mixtures thereof and an acid fraction comprising $C_1$ to $C_6$ monocarboxylic and dicarboxylic acids, substantially adipic acid and 6-hydroxyhexanoic acid and also 1,4-dihydroxycyclohexane and/or precurrors thereof;
    c. said acid fraction is esterified by reacting same in the liquid phase with a $C_2$-$C_{10}$ monohydric or dihydric alkane alcohol under esterification conditions so as to esterify at least a portion of the adipic acid and 6-hydroxyhexanoic acid contained in said acid fraction;
    d. the ester product obtained by esterifying said acid fraction is reacted while in a liquid phase with molecular hydrogen under hydrogenolysis conditions including elevated temperature and superatmospheric pressure and in the presence of a catalytic amount of a hydrogenolysis catalyst to hydrogenolyze the esters of adipic acid and 6-hydroxyhexanoic acid so as to form 1,6-hexanediol and said alkane alcohol; and
    e. separating 1,6-hexanediol from the product of said hydrogenolysis;
    the improvement which comprises a prehydrogenation of said acid fraction prior to esterification thereof by reacting said acid fraction while in a liquid phase with molecular hydrogen at temperatures within the range of about 100° to 350°C and pressures within the range of about 50 to 400 atmospheres absolute, and in the presence of a metallic hydrogenation catalyst of copper, cobalt, platinum or palladium or mixtures thereof sufficient to convert a substantial portion of said 1,4-dihydroxycyclohexane to cyclohexanol, cyclohexane and/or cyclohexene, but insufficient to appreciably hydrogenolyze the adipic acid and 6-hydroxyhexanoic acid therein.

2. The process of claim 1 wherein said prehydrogenation of said acid fraction is accomplished at temperatures within the range of about 150° to 275°C and at pressures within the range of about 70 to 300 atmospheres absolute, and wherein said alkane alcohol is a $C_3$-$C_{10}$ alkanediol.

3. The process of claim 1 wherein the hydrogenation catalyst used for the prehydrogenation of said acid fraction is a metallic copper catalyst.

4. The process of claim 1 wherein the hydrogenation catalyst used for the prehydrogenation of said acid fraction is a metallic platinum catalyst.

5. The process of claim 2 wherein the hydrogenation catalyst used for the prehydrogenation of said acid fraction is a metallic copper catalyst.

6. The process of claim 2 wherein the hydrogenation catalyst used for the prehydrogenation of said acid fraction is a metallic platinum catalyst.

* * * * *